(12) United States Patent
Malak

(10) Patent No.: US 7,492,458 B2
(45) Date of Patent: Feb. 17, 2009

(54) PLASMON-ENHANCED DISPLAY TECHNOLOGIES

(75) Inventor: Henryk Malak, Ellicott City, MD (US)

(73) Assignee: American Environmental Systems, Inc., Ellicott City, MD (US)

( * ) Notice: Subject to any disclaimer, the term of this patent is extended or adjusted under 35 U.S.C. 154(b) by 329 days.

(21) Appl. No.: 11/029,258

(22) Filed: Jan. 5, 2005

(65) Prior Publication Data

US 2005/0146724 A1 Jul. 7, 2005

Related U.S. Application Data

(60) Provisional application No. 60/534,136, filed on Jan. 5, 2004.

(51) Int. Cl.
*G01N 21/55* (2006.01)

(52) U.S. Cl. ..................................................... 356/445

(58) Field of Classification Search .................. 356/445, 356/317, 301, 417; 422/82.05; 427/250, 427/596

See application file for complete search history.

(56) References Cited

U.S. PATENT DOCUMENTS 6,424,418 B2 * 7/2002 Kawabata et al. ........... 356/445
2006/0256331 A1 * 11/2006 Lakowicz et al. ........... 356/317

* cited by examiner

*Primary Examiner*—Gregory J Toatley, Jr.
*Assistant Examiner*—Abdullahi Nur

(57) ABSTRACT

This invention describes a method of use surface plasmon of nanoparticles to enhance CRT, LCD, OLED, Plasma and other display technologies. The plasmon-enhanced nanoparticles interacting with nearby luminophores, liquid crystals or other materials improve in display technologies brightness, contrast, and longevity of luminophores; make faster response time and better direction emission display. The plasmon-enhanced nanoparticles like quantum dots can be also used directly as a luminophores in quantum display technologies.

13 Claims, No Drawings

PLASMON-ENHANCED DISPLAY TECHNOLOGIES

CROSS REFERENCE TO RELATED APPLICATIONS

This application is related to U.S. Provisional Patent Application No. 60/534,136 entitled "Plasmon Enhanced Display Technologies" filed Jan. 5, 2004, which are herein incorporated by reference.

STATEMENT REGARDING FEDERALLY SPONSORED RESEARCH

There is NO claim for federal support in research or development of this product.

FIELD OF THE INVENTION

The invention relates to a method of the use nanotechnology advances in display technologies.

BACKGROUND OF THE INVENTION

Current CRT and Plasma Display technologies mainly are based on luminophores, e.g. fluorophores and phosphors substances. The luminescence quantum yields of these substances are relatively high, however they photobleach and causing decreasing brightness, contrast and colors over usage time. Therefore exist great need to improve luminophores performance in display technologies.

Another problem with current Liquid Crystal Display (LCD) technologies is slow response time, usually milliseconds and longer, at each displayed pixel. This cause that the LCD resolution suffer in fast moving displayed objects. Again, exist great need to make faster response in LCD technologies.

Up to this date there is not described a method of the use surface plasmon of nanoparticles to enhance display technologies.

REFERENCES

The following are scientific reports found that may be associated within the herein disclosed invention.

Y. Sun and Y. Xia, "Increased Sensitivity of Surface Plasmon Resonance of Gold Nanoshells Compared to That of Gold Solid Colloids in Response to Environmental Changes", Anal. Chem., 74, 5297-5305 (2002)

Cao, Y.; Jin, R.; Mirkin, C. A. *J. Am. Chem. Soc.,* 123, 7961 (2001)

M. Kerker, "Optics of colloid silver", *J. Colloid Interface Sci.* 105, 298 (1985)

Lakowicz et al, "Intrinsic fluorescence from DNA can be enhanced by metallic particles", *Biochem. Biophys. Res. Comm.* 286, 875 (2001)

Gryczynski et al., "Multiphoton excitation of fluorescence near metallic particles: enhanced and localized excitation", *J. Phys. Chem. B,* 106, 2191 (2002)

M. Moskovits: *Rev. Mod. Phys.* 57, 783 (1985)

T. L. Haslett, L. Tay, M. Moskovits: J. Chem. Phys. 113, 1641 (2000), and references therein K. Kneipp, Y. Wang, H. Kneipp, L. T. Perelman, I. Itzkan, R. R. Dasari, M. S. Feld: *Phys. Rev. Lett.* 78, 1667 (1997)

Ditlbacher H. et al., *Appl. Phys.* B 73, 373-377 (2001)

SUMMARY OF THE INVENTION

This invention describes a method of use surface plasmon of nanoparticles to enhance CRT, LCD, Plasma and other display technologies. The plasmon-enhanced nanoparticles interacting with nearby luminophores, liquid crystals or other materials improve in display technologies brightness, contrast, and longevity of luminophores; make faster response time and better directional emission display. The plasmon-enhanced nanoparticles like quantum dots can be also used directly as a luminophores in display technologies.

DETAIL DESCRIPTION OF THE INVENTION

1. Abbreviations and Definitions

LCD—liquid crystal display

CRT—cathode-ray tube

LED—light emitting diode

OLED—organic light emitting diode

SPR—surface plasmon resonance generated in a nanoparticle under illumination by electromagnetic radiation and other forms of energy one-photon mode of excitation—process in which molecule is excited by a one photon absorption event two-photon mode of excitation—process in which molecule is excited by simultaneous absorption of two photons multi-photon mode of excitation—process in which molecule is excited by simultaneous absorption of three or more photons step-wise mode of excitation—process in which molecule is excited by absorption of one photon and subsequently by absorption of second photon up-conversion mode of excitation—process in which a molecule is excited by lower energy photon than energy of the lowest excited state of the molecule metal island—a nanoparticle on a substrate without defined shape quantum dot—a nanoparticle, which size is a few nanometers and exhibit luminescence properties.

2. Exemplary Embodiments

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

The present invention provides a novel methodology and applications that overcome limitations of conventional methods of using luminophores or liquid crystals in display technologies.

The invention relates to scientific findings of the surface plasmon resonance (SPR)-enhanced interaction between metal nanoparticles and nearby molecules, which were published in few scientific reports (M. Kerker, "Optics of colloid silver", *J. Colloid Interface Sci.* 105, 298 (1985); Lakowicz et al, "Intrinsic fluorescence from DNA can be enhanced by metallic particles", *Biochem. Biophys. Res. Comm.* 286, 875 (2001); Gryczynski et al., "Multiphoton excitation of fluorescence near metallic particles: enhanced and localized excitation", *J. Phys. Chem. B,* 106, 2191 (2002)). In these reports, researchers used the fluorophores (mostly organic laser dyes) to visualize or test the SPR-enhanced interactions. Their studies show that the fluorescence intensity of the fluorophores located nearby metal nanoparticles can be enhanced by a factor as high as $\sim 10^4$ with one-photon mode of excitation and $\sim 10^8$ with two-photon mode of excitation, and Raman signal for fluorophores which are in contact with metal nanoparticle can be enhanced by $\sim 10^{14}$ (M. Moskovits: *Rev. Mod. Phys.* 57, 783 (1985); T. L. Haslett, L. Tay, M. Moskovits: J. Chem. Phys. 113, 1641 (2000), and references therein; K. Kneipp, Y.

Wang, H. Kneipp, L. T. Perelman, I. Itzkan, R. R. Dasari, M. S. Feld: *Phys. Rev. Lett.* 78, 1667 (1997); Gryczynski et al., "Multiphoton excitation of fluorescence near metallic particles: enhanced and localized excitation", *J. Phys. Chem. B*, 106, 2191 (2002)). The observed SPR-enhanced interaction of metal nanoparticles with fluorophores was also associated with intense decomposition of fluorophores when fluorophores where at a distance of 20 nm or less from metal nanoparticles (Ditlbacher H. et al., *Appl. Phys.* B 73, 373-377 (2001)). At the larger distances than 20 nm the fluorescence lifetime of fluorophores interacting with plasmon nanoparticles was decreasing and fluorophores longevity was significantly increased (Lakowicz et al, "Intrinsic fluorescence from DNA can be enhanced by metallic particles", *Biochem. Biophys. Res. Comm.* 286, 875 (2001)). The present invention expands the above scientific findings to new methods and new applications of the SPR-enhanced interactions of nanoparticles embedded into a material with the nearby luminophores and with the material. These new applications relate to the method of the use SPR in display technologies. The luminescence quantum yield and longevity of plasmon-enhanced fluorophores can be significantly improved which is needed in CRT, plasma and other display technologies.

In the invention one of the embodiments uses quantum dots for enhancing display technologies. The quantum dots are made of semiconductor or metal and they are highly fluorescent fluorophores. The emitted color by quantum dot depends on size of a quantum dots cluster. Typically, the size of the quantum dot cluster is in a few nanometers range. There are many advantages of using quantum dots in display technologies, like minimizing photobleaching effect; improving brightness, contrast and spatial resolution; improving polarization and directivity of emitted light; decreasing time response; increasing number of colors use in display and significant saving energy consumption, but not limited to them.

Anyone of ordinary skill in the art will appreciate the use plasmon-enhanced nanoparticles to decrease a response time of each pixel in LCD technologies. In the LCD technology one of major problem is decreased image resolution by slow response time at each pixel. We propose to embed nanoparticles to liquid crystal and use plasmon absorption of these nanoparticle to increase temperature of liquid crystal. The increased temperature of liquid crystal will lead to faster response at each pixel of display. In addition, spectral and physical properties of nanoparticles can be use to improve a spatial resolution and colors of display.

Another embodiment in the present invention is the use SPR of nanoparticles to enhance absorption and emission of phosphors used in Plasma Display technologies. The cross-sections for absorption of phosphors are not as high as metal or semiconductor nanoparticles. Therefore, number of phosphor molecules emitting light after plasma discharge in a plasma display cell is smaller than in a proposed method of mediated absorption by the nanoparticle. In this embodiment, the nanoparticles are placed nearby phosphors in the cell, and plasma discharge light absorbed efficiently by nanoparticles is energy transfer to phosphors, which they next emit light. In that method, brightness of plasma display may increase few orders of magnitude and it is expected significant increase longevity of phosphors. The response time of phosphors will be decreased too. Another embodiment in the present invention is the use SPR for a time-resolved display. An interaction of SPR with luminophores cause not only increasing luminescence intensity of luminophores but also shortening their luminescence lifetimes. Luminescence lifetime of luminophore depends on a distance of luminophore from SPR-enhanced nanoparticle and this lifetime can be within a range of picoseconds to milliseconds. Therefore by controlling the distance the time-resolved display can be created. This invention can lead to display technologies in which multiple images in different time can be displayed on the same display unit, and the images can be retrieved by well-known time gating techniques.

What is claimed is:

1. A method of using nanoparticles in a display technology comprising steps of: providing a nanoparticle capable to luminesce of characteristic spectral electromagnetic radiation when the nanoparticle is excited by a surface plasmon resonance source; and exciting the nanoparticle by the surface plasmon resonance source to luminesce characteristic spectral electromagnetic radiation.

2. A method of claim 1, wherein the nanoparticle is a metal, metal oxide, metal dioxide, metallic salt, intermetallic alloy, transition metal, electric conductor, electric superconductor, electric semiconductor, electric semiconductor doped with metal, quantum dot, dielectric, alkaline earth metal, earth rare element, or carbon nanotube.

3. The method of claim 1, wherein the nanoparticle is a thin film, colloid, fiber, metal island, nanowire, nanotube, empty shell, shell filled with a conducting material, shell filled with a dielectric material, or shell filled with a semiconductor material.

4. The method of claim 2, wherein the nanoparticle is uncoated or coated by a material selected from the group of: semiconductor, conductor, organic substance, liquid crystal substance, inorganic substance, polymer, light sensitive polymer, environmentally sensitive polymer.

5. The method of claim 1, wherein the method further comprising a molecule, wherein the molecule is excited by the nanoparticle and emit luminescence.

6. The method of claim 1, wherein the nanoparticle has plurality of the nanoparticles.

7. The method of claim 1, wherein the plasmon source comprises a single or a multiple energy source of polarized electromagnetic radiation, single or multiple energy source of none-polarized electromagnetic radiation source, ultrasound source, electrochemical source, electric source, electrostatic source, or magnetic source.

8. The method of claim 7, wherein the electromagnetic radiation source is selected from the group consisting of a laser with single wavelength, laser with plurality wavelengths, semiconductor laser, pulsed laser, Q-switched laser, light emitted diode, lamp, organic light emitted diode, plasma or X-Rays.

9. The method of claim 8, wherein said electromagnetic radiation source has a wavelength or wavelengths within a range of 0.001 nm to 20,000 nm.

10. A method of claim 1, wherein the composition is excited in a one-photon mode, two-photon mode, multi-photon mode, step-wise mode, up-conversion mode, harmonic generation mode, or light scattering mode.

11. A method of claim 1, wherein the display technology is a LCD technology, CRT technology, OLED technology, LED technology, plasma display technology, CMOS technology, CCD technology, or phosphoroscopy technology.

12. A method of claim 1 is used to enhance the display technology by improving brightness of luminophores, longevity of luminophores, shorten luminescence lifetime of luminophores, improving directional display, improving contrast display, shorten time response of each display pixel, improving three-dimensional and holographic displays, improving polarization display, improving spatial resolution display, increasing number of displayed colors, improving energy saving, improving three-dimensional display, or enhancing plasma discharge excitation of luminophores.

13. A method of claim 1, wherein the method is further used in time-resolved display technologies.

* * * * *